(12) United States Patent
Rubinstein et al.

(10) Patent No.: US 8,293,706 B2
(45) Date of Patent: Oct. 23, 2012

(54) METHOD FOR INHIBITING RELEASE OF HEPATITIS B VIRUS FROM LIVER CELLS

(76) Inventors: Menachem Rubinstein, Rehovot (IL); Ariel Werman, Jerusalem (IL); Ben Alkahe, Tel-Aviv (IL)

( * ) Notice: Subject to any disclaimer, the term of this patent is extended or adjusted under 35 U.S.C. 154(b) by 0 days.

(21) Appl. No.: 12/811,912

(22) PCT Filed: Jan. 7, 2009

(86) PCT No.: PCT/IL2009/000023
§ 371 (c)(1),
(2), (4) Date: Jul. 7, 2010

(87) PCT Pub. No.: WO2009/087622
PCT Pub. Date: Jul. 16, 2009

(65) Prior Publication Data
US 2010/0279928 A1    Nov. 4, 2010

(30) Foreign Application Priority Data
Jan. 7, 2008 (IL) .......................... 188628

(51) Int. Cl.
*A01N 37/18* (2006.01)
*A61K 38/00* (2006.01)
*A61P 1/16* (2006.01)
*C07K 1/00* (2006.01)
*C07K 14/00* (2006.01)
*C07K 17/00* (2006.01)
*C12P 21/08* (2006.01)

(52) U.S. Cl. .................. 514/4.3; 530/350; 530/387.3

(58) Field of Classification Search .................. None
See application file for complete search history.

(56) References Cited

U.S. PATENT DOCUMENTS 6,365,713 B1 * 4/2002 Rubinstein et al. .......... 530/350
6,849,720 B2 * 2/2005 Yonah et al. ............. 530/388.22

FOREIGN PATENT DOCUMENTS
EP         0553667 A1    1/1993

OTHER PUBLICATIONS

Agnello et al. Hepatitis C virus and other flaviviridae viruses enter cells via low density lipoprotein receptor, Proc. Natl Acad Sci USA, 96(22):12766-71 (1999).
Fischer et al., An antiviral soluble form of the LDL receptor induced by interferon, Science, 262:250-253 (1993).
Goldstein et al., Coated pits, coated vesicles, and receptor-mediated endocytosis, Nature, 279:679-685 (1979).
Yamamoto et al., The human LDL receptor: A cysteine-rich protein with multiple Alu sequences in its mRNA, Cell, 39:27-38 (1984).
Yamamoto et al., Characterization of low density lipoprotein receptor ligand interactions by fluorescence resonance energy transfer, Journal of Lipid Research, 47:1091-1096 (2006).
Yamamoto et al., Apolipoprotein E isoform-specific binding to the low-density lipoprotein receptor, Analytical Biochemistry, 372:222-226 (2008).

* cited by examiner

*Primary Examiner* — Robert Landsman
(74) *Attorney, Agent, or Firm* — Browdy and Neimark, PLLC

(57) ABSTRACT

The invention relates to the use of the souluble LDL receptor (sLDLR) in viral hepatitis.

17 Claims, No Drawings

METHOD FOR INHIBITING RELEASE OF HEPATITIS B VIRUS FROM LIVER CELLS

FIELD OF THE INVENTION

The present invention relates to the therapeutical use of the soluble LDL receptor (sLDLR) in viral hepatitis, especially HBV infection.

BACKGROUND OF THE INVENTION

Cholesterol, a component of all eukaryotic plasma membranes, is essential for the growth and viability of cells in higher organisms. However, high serum levels of cholesterol cause disease and death by contributing to the formation of atherosclerotic plaques in arteries throughout the body. The major site of cholesterol synthesis in mammals is the liver. Appreciable amounts of cholesterol are also formed by the intestine. The rate of cholesterol formation by these organs is highly responsive to the amount of cholesterol absorbed from dietary sources. Cells outside of the liver and intestine acquire cholesterol from the plasma rather than by synthesising it de novo. Cholesterol and other lipids are transported in body fluids by lipoproteins, which are classified according to increasing density. A lipoprotein is a particle consisting of a core of hydrophobic lipids surrounded by a shell of polar lipids and apoproteins. These lipoproteins have two roles: they solubilize highly hydrophobic lipids and they contain signals that regulate the movement of particular lipids in and out of specific target cells and tissues. Cholesterol is transported in body fluids by low-density lipoproteins (LDL) which binds to a specific receptor on the plasma membrane of non hepatic cells. The receptor-LDL complex is then internalised into the cells by a transport mechanism known as receptor mediated endocytosis (Goldstein et al. 1979). The low density lipoprotein (LDL) receptor is the prototype of a family of structurally related cell surface receptors that mediate endocytosis of multiple ligands in mammalian cells.

The nucleotide sequence of a cloned 5.3 kilobase cDNA for the human LDL receptor revealed five structural domains, some of which share sequence homology with other proteins. Its $NH_2$-terminal ligand-binding domain consists of 322 residues, which include 47 cysteine residues. This domain is followed by four additional domains: the first consists of about 350 amino acid residues and is homologous to the EGF receptor, the second consists of 48 amino acid residues rich in O-linked sugars, the third is a single trans-membrane domain of 22 amino acid residues and the fourth is a cytoplasmic domain of 50 amino acid residues (Yamamoto et al 1984).

A soluble form of the LDLR exhibiting antiviral activity, sLDLR, was identified and isolated from the culture supernatant of interferon-induced cells (Fischer et al. 1993) and in body fluids (Fischer et al. 1994). Several interferon-induced proteins have been identified that are instrumental in the induction of the antiviral state by IFNs. One such protein exhibiting antiviral activity was produced and accumulated in the culture supernatant of human amnion WISH cells. This protein was purified to homogeneity and identified as the sLDLR (see EP 0 553 667 and Fischer et al. 1993). The sLDLR was found to be secreted into the medium by mammalian cells that enter an antiviral state in response to interferon. In contrast to interferon, sLDLR does not induce an antiviral state in the cells but is antiviral by itself. It was found that sLDLR apparently has to be present throughout the process of viral replication maturation and budding suggesting it might be involved in a complex process that leads to the inhibition of virus assembly or budding (unpublished data).

Endocytosis of the hepatitis C virus has been recently shown to be mediated by LDL receptors on cultured cells (Agnello et al. 1999).

Liver damage or injury may have diverse causes. It may be due to viral or bacterial infections, alcohol abuse, immunological disorders, or cancer, for example.

Viral hepatitis, due to Hepatitis B virus and Hepatitis C virus are poorly managed diseases that afflict large number of people world-wide. The number of known hepatitis viruses known is constantly increasing. Apart from Hepatitis B and C virus, at least four other viruses causing virus-associated hepatitis have been discovered so far, called Hepatitis A, D, E and G-Virus.

Lamivudine (3TC), trade name Epivir, an anti HIV treatment, is also approved for the treatment of hepatitis B. Studies have shown that Epivir can reduce the amount of hepatitis B virus to very low levels, although this effect does not always last.

Adefovir Dipovoxil (ADV) is another HIV treatment that has been shown to be effective in chronic hepatitis B.

SUMMARY OF THE INVENTION

The present invention is based on the finding that sLDLR is effective for treatment and/or prevention of liver infections caused by HBV.

It is a first object of the present invention to provide for a novel means for treating and/or preventing liver infections caused by HBV. The invention therefore relates to the use of a sLDLR for the manufacture of a medicament for treatment and/or prevention of viral hepatitis, caused by HBV.

In order to apply gene therapeutical approaches to deliver the sLDLR to the liver, further aspects of the invention relate to the use of expression vectors comprising the coding sequence of an sLDLR for the treatment and/or prevention of the disease conditions. The invention further relates to the use of endogenous gene activation of sLDLRs and to the use of cells genetically engineered to express sLDLRs for the prevention and/or treatment of liver infection caused by HBV.

DESCRIPTION OF THE INVENTION

The present invention is based on the finding of a beneficial effect of a sLDLR in viral hepatitis, in particular hepatitis caused by the HBV virus.

According to the first aspect of the present invention, sLDLR is used for the manufacture of a medicament for treatment and/or prevention of viral liver infection caused by HBV.

According to the invention, sLDLRs are also used for the manufacture of a medicament for treatment and/or prevention of chronic active hepatitis, also called chronic aggressive hepatitis. It is a continuing inflammation of the liver that damages the liver cells. Causes of chronic active hepatitis include viral infection and others. The disease is characterized by necrosis or death of liver cells, active inflammation, and fibrosis that may lead to liver failure, cirrhosis, and death. The incidence is 1 out of 10,000 people. Risk factors are autoimmune diseases, previous infection with hepatitis C, or a positive hepatitis A or hepatitis B antigen for over 6 months.

Chronic persistent hepatitis is a mild, nonprogressive form of liver inflammation, and it is also a disease encompassed by the term "liver infection" according to the present invention.

Examples of production of amino acid substitutions in proteins which can be used for obtaining muteins of sLDLR polypeptides or proteins for use in the present invention include any known method steps, such as presented in U.S.

Pat. Nos. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904, 584 (Shaw et al).

The term "fused protein" refers to a polypeptide comprising an sLDLR, or a viral SLDLR, or a mutein or fragment thereof, fused with another protein, which, e.g., has an extended residence time in body fluids. A sLDLR may thus be fused to another protein, polypeptide or the like; e.g., an immunoglobulin or a fragment thereof.

"Functional derivatives" as used herein cover derivatives of sLDLRs and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of sLDLR and do not confer toxic properties on compositions containing it.

These derivatives may, for example, include polyethylene glycol side-chains, which may mask antigenic sites and extend the residence of an sLDLR in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of an sLDLR muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to sLDLR.

In a highly preferred embodiment of the present invention, the sLDLR employed is a sLDLR, or an isoform, a mutein, fused protein, functional derivative, active fraction or circularly permutated derivative thereof. These isoforms, muteins, fused proteins or functional derivatives retain the biological activity of sLDLR and preferably have essentially at least an activity similar to sLDLR. Ideally; such proteins have a biological activity which is even increased in comparison to unmodified sLDLR. Preferred active fractions have an activity which is better than the activity of sLDLR, or which have further advantages, like a better stability or a lower toxicity or immunogenicity, or they are easier to produce in large quantities, or easier to purify.

Functional derivatives of sLDLR may be conjugated to polymers in order to improve the properties of the protein, such as the stability, half-life, bioavailability, tolerance by the human body, or immunogenicity. To achieve this goal, sLDLR may be linked e.g. to polyethlyenglycol (PEG). PEGylation may be carried out by known methods, described in WO 92/13095, for example.

Therefore, in a preferred embodiment of the present invention, the sLDLR employed is PEGylated.

In a further preferred embodiment of the invention, the sLDLR employed is a fused protein comprising all or part of a sLDLR, which is fused to all or part of an immunoglobulin. The person skilled in the art will understand that the resulting fusion protein retains the biological activity of sLDLR. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO:1) introduced between the SLDLR sequence and the immunoglobulin sequence. The resulting fusion protein has improved properties, such as an extended residence time in body fluids (half-life), increased specific activity, increased expression level, or the purification of the fusion protein is facilitated.

In a preferred embodiment, sLDLR is fused to the constant region of an Ig molecule. Preferably, it is fused to heavy chain regions, like the CH2 and CH3 domains of human IgG1, for example. The generation of specific fusion proteins comprising sLDLR and a portion of an immunoglobulin are described in example 11 of WP99/09063, for example. Other isoforms of Ig molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

In a preferred embodiment of the present invention, the sLDLR is used in an amount of about 0.0001 to 10 mg/kg of body weight, or about 0.01 to 5 mg/kg of body weight or about 0.1 to 3 mg/kg of body weight or about 1 to 2 mg/kg of body weight. In yet a further preferred embodiment, the sLDLR is used in an amount of about 0.1 to 1000 µg/kg of body weight or 1 to 100 µg/kg of body weight or about 10 to 50 µg/kg of body weight.

The invention further relates to the use of an expression vector comprising the coding sequence of an sLDLR in the preparation of a medicament for the prevention and/or treatment of liver infection. A gene therapeutical approach is thus used for treating and/or preventing the disease. Advantageously, the expression of the sLDLR will then be in situ.

The invention further relates to the use of a cell that has been genetically modified to produce an sLDLR in the manufacture of a medicament for the treatment and/or prevention of liver infection, arthritis or inflammatory bowel disease.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector) which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active protein(s) according to the invention can also be ameliorated by using conjugation procedures which increase the half-life of the molecule in the human body, for example linking the molecule to polyethylenglycol, as described in the PCT Patent Application WO 92/13095.

The therapeutically effective amounts of the active protein(s) will be a function of many variables, including the type of antagonist, the affinity of the antagonist for IL-18, any residual cytotoxic activity exhibited by the antagonists, the route of administration, the clinical condition of the patient (including the desirability of maintaining a non-toxic level of endogenous IL-18 activity A "therapeutically effective amount" is such that when administered, the sLDLR results in inhibition of the HBV virus. The dosage administered, as single or multiple doses, to an individual will vary depending upon a variety of factors, including sLDLR pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of IL-18 in an individual.

According to the invention, the sLDLR is used in an amount of about 0.0001 to 10 mg/kg or about 0.01 to 5 mg/kg or body weight, or about 0.01 to 5 mg/kg of body weight or about 0.1 to 3 mg/kg of body weight or about 1 to 2 mg/kg of body weight. Further preferred amounts of the sLDLRs are amounts of about 0.1 to 1000 µg/kg of body weight or about 1 to 100 µg/kg of body weight or about 10 to 50 µg/kg of body weight.

The route of administration which is preferred according to the invention is administration by subcutaneous route. Intramuscular administration is further preferred according to the invention.

In further preferred embodiments, the sLDLR is administered daily or every other day.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the sLDLR can be administered prophylactically or therapeutically to an individual prior to, simultaneously or sequentially with other therapeutic regimens or agents (e.g. multiple drug regimens), in a therapeutically effective amount, as determined by the physician according to the effectiveness of the regimen. Active agents that are administered simultaneously with other therapeutic agents can be administered in the same or different compositions.

Having now described the invention, it will be more readily understood by reference to the following examples that are provided by way of illustration and are not intended to be limiting of the present invention.

EXAMPLES

Example 1

Preparation of sLDLR 1.1. PCR Amplification of HSLDLR Fragments

The +292 and +331 fragments LDLR genes were isolated by PCR amplification using the entire LDLR gene as template. Amplification was performed in reaction mixtures containing 1 ng of the template, 400 ng of each primer (see section 6.1), 0.2 mM dNTP mix, 2 mM $MgCl_2$, 5 U Pfu DNA polymerase (Stratagene), in the buffer supplied with the enzyme, in a total reaction volume of 100 µl. 31 thermal cycles were employed (1 min 94° C., 1 min 65° C., 2 min 72° C.), preceded by 2 min heating at 94° C. and followed by 10 min at 72° C.

1.2. Preparation of Plasmid DNA

Plasmid DNA was prepared using a commercially available kit (Qiagen DNA Maxi Kit Cat. 12162), according to the procedure described by the manufacturer.

1.3. Transfection and Gene Amplification

CHO-DUKX cells (deficient in DHFR activity) were grown in F12 supplemented with 10% FBS. Transfection was performed by cationic liposomes using LipofectAmine (Gibco BRL), according to the protocol described by the manufacturer. Seventy-two hours following transfection the cells were transferred to a selective medium. Cells expressing the DHFR activity formed colonies, which were isolated by lifting the cells with trypsin-soaked paper discs, and screened for r-hsLDLR activity.

Gene amplification was performed according to the following procedure:

Clones that grew in the selective medium (positive DHFR activity) were seeded at a low density (4000 cells/$cm^2$) into 5-6 T-flasks, each containing increasing concentrations of methotrexate, ranging from 0 (as a control) to 100 nM.

1. About 10 days after exposure to MTX, resistant colonies could be microscopically visualized in part of the T-flasks. Cultures that exhibited about 10% cell survival were chosen for the next amplification step.
2. The cells were re-seeded at a low density (4000 cells/$cm^2$) into 5-6 T-flasks, each containing a different concentration of methotrexate. Cells were reseeded in increasing MTX concentrations ranging from the concentration chosen in step 1 (lowest concentration) to ten times the chosen concentration (highest concentration).
3. Steps 1-2 were repeated for the next amplification rounds.
4. After the last round of gene amplification, the cells were subcloned by limiting dilution.
5. r-hsLDLR was obtained from the cells by conventional methods.

1.4. Bioassay

A semi-quantitative bioassay was used to monitor the product throughout the development stages. The assay was a CPE inhibition assay, similar to the bioassay used for IFN-β. In the initial stages of the development, IFN-β was used as a standard. It was later replaced by a batch of purified r-hsLDLR.

WISH cells were cultured in 1×MEM supplemented with 10% FBS and 4 mM glutamine in a 37 C.°, 5% $CO_2$ incubator. Twenty-four hours before the assay, exponentially growing cells were seeded in 96-well TC plates, at a density of 40,000 cells/well. Samples to be tested and the standard were diluted and dispensed into the cells-containing wells. VSV was immediately added to the wells, at a MOI of 0.5 pfu/cell. The plates were incubated 16-18 hours at 37 C.° and were then washed with ethanol. The monolayer of surviving cells was observed by Gram Crystal Violet stain. Quantitation of the cytopathic effect relative to the standard was performed by plotting the colour density versus standard concentration.

Example 2

Inhibition of HBV Release from Virus-Infected Hepatoma Cells

The ability of sLDLR to inhibit pathogenic viruses was tested by the NIAID Antimicrobial Acquisition and Coordinating Facility (AACF). Confluent cultures of 2.2.15 cells (HBV-infected human HepG2 hepatocellular carcinoma cells (ATCC HB-8065), constitutively shedding HBV virions) were maintained on 96-well flat-bottomed tissue culture plates in RPMI1640 medium with 2% fetal bovine serum (Korba & Gerin, Antivir. Res. 19:55-70, 1992). Cultures (6 per each of 4 test concentrations on two replicate plates) were treated with 9 consecutive daily doses of sLDL compounds. Medium was changed daily with fresh test compounds. HBV virion DNA in the culture medium was assessed 24 hours after the last treatment by quantitative blot hybridization. Uptake of neutral red dye (absorbance of internalized dye at 510 nM [A510]) wa used to determine the relative level of toxicity 24 hours following the last treatment (Korba & Gerin, Antivir. Res. 19:55-70, 1992). Values are presented as a percentage of the average A510 values for 9 separate cultures of untreated cells maintained on the same plate. Cultures for the toxicity analyses were seeded at the same time with the identical pool of stock cells used for the antiviral analyses and maintained in an identical manner. A total of 3 cultures were treated with each concentration of test compound. Toxicity analyses utilized 10-fold higher levels of test compounds (with 3-fold serial dilutions). CC50, EC50, EC90, and S.I. (CC50/EC90) were calculated. Lamivudine (3TC) was used as a positive assay control. The following results were obtained:

| sLDLR ug/ml | | | | Lamivudine uM | | | |
|---|---|---|---|---|---|---|---|
| CC50 | EC50 | EC90 | SI | CC50 | EC50 | EC90 | SI |
| >10 | 0.131 | 0.922 | >11 | 2308 | 0.045 | 0.146 | 15178 |

Thus, sLDLR inhibited the formation of HBV virion from virus-infected cells at concentrations far below toxicity.

Further tests carried out with sLDLR showed that it was active against all tested lamivudine as well as adefovir dipovoxil resistant mutants, as shown in the table below.

| ARB # | Cmpd Name | Virus | Assay Type | Drug Strain | Units | EC50 | EC90 | Control: 3TC (µM) EC50 | EC90 | Control: ADV (µM) EC50 | EC90 |
|---|---|---|---|---|---|---|---|---|---|---|---|
| 07-000023 | MRAWBA | HBV | HBVDR | WT | uM | 0.9 | 6 | 0.2 | 0.7 | 1.5 | 6.5 |
| | | HBV | HBVDR | L180M | uM | 0.8 | 6.3 | 5.2 | 20 | 1.9 | 8.5 |
| | | HBV | HBVDR | M204V | uM | 1 | 6.5 | >100 | >100 | 1.8 | 7 |
| | | HBV | HBVDR | M204I | uM | 1.1 | 8 | >100 | >100 | 1.3 | 7.2 |
| | | HBV | HBVDR | LM/MV | uM | 1.2 | 7.5 | >100 | >100 | 1.3 | 7.8 |
| | | HBV | HBVDR | N236T | uM | 1 | 8.2 | 0.2 | 0.6 | 8.1 | 32 |

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

Agnello et al, (1999), PNAS, 96:12766-12771
Fischer et al, (1993), Science, Vol. 262, 250-253
Goldstein et al (1979), Nature 279, 679-685
Yamamoto et al, (1984), Cell, Vol. 39, 27-38

The invention claimed is:

1. A method for inhibiting hepatitis B virus (HBV) release from HBV infected liver cells, comprising administering an effective inhibiting amount of soluble low density lipoprotein receptor (sLDLR) to a patient in need thereof to inhibit HBV release from HBV infected liver cells.

2. The method of claim 1, wherein the sLDLR is sLDLR or an isoform or fused protein of sLDLR.

3. The method of claim 2, wherein the sLDLR is PEGylated.

4. The method of claim 2, wherein the fused protein of sLDLR is a fusion of sLDLR to an immunoglobulin or an immunoglobulin fragment.

5. The method of claim 4, wherein the fused protein comprises the constant region of an immunoglobulin or a fragment of the immunoglobulin constant region.

6. The method of claim 5, wherein the immunoglobulin is of the IgG1 or IgG2 isotype.

7. The method of claim 1, wherein the sLDLR is used in an amount of about 0.0001 to 10 mg/kg of body weight.

8. The method of claim 1, wherein the sLDLR is used in an amount of about 0.1 to 1000 µg/kg of body weight.

9. The method of claim 1, wherein the sLDLR is administered subcutaneously.

10. The method of claim 1, wherein the sLDLR is administered intramuscularly.

11. The method of claim 1, wherein the sLDLR is administered daily.

12. The method of claim 1, wherein the sLDLR is administered every other day.

13. The method of claim 1, wherein the sLDLR is used in an amount of about 0.01 to 5 mg/kg of body weight.

14. The method of claim 1, wherein the sLDLR is used in an amount of about 0.1 to 3 mg/kg of body weight.

15. The method of claim 1, wherein the sLDLR is used in an amount of about 1 to 2 mg/kg of body weight.

16. The method of claim 1, wherein the sLDLR is used in an amount of about 1 to 100 µg/kg of body weight.

17. The method of claim 1, wherein the sLDLR is used in an amount of about 10 to 50 µg/kg of body weight.

* * * * *

UNITED STATES PATENT AND TRADEMARK OFFICE
CERTIFICATE OF CORRECTION

PATENT NO. : 8,293,706 B2
APPLICATION NO. : 12/811912
DATED : October 23, 2012
INVENTOR(S) : Rubinstein et al.

Page 1 of 1

It is certified that error appears in the above-identified patent and that said Letters Patent is hereby corrected as shown below:

On the cover of the issued patent, above "(*) Notice" add --(73) Assignee YEDA RESEARCH AND DEVELOPMENT CO., LTD. Rehovot (IL)--

Signed and Sealed this
Fourth Day of December, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence

```
<220> FEATURE:
<223> OTHER INFORMATION: Synthetic

<400> SEQUENCE: 1

Glu Phe Gly Ala Gly Leu Val Leu Gly Gly Gln Phe Met
1               5                   10
```